United States Patent [19]
Yoshimura et al.

[11] 4,301,083
[45] Nov. 17, 1981

[54] PREPARATION OF ETHERIFIED POLYOXYALKYLENE DERIVATIVES

[75] Inventors: Noriaki Yoshimura; Masuhiko Tamura, both of Kurashiki, Japan

[73] Assignee: Kuraray Co., Ltd., Kurashiki, Japan

[21] Appl. No.: 109,065

[22] Filed: Jan. 2, 1980

Related U.S. Application Data

[63] Continuation of Ser. No. 867,621, Jan. 6, 1978, abandoned.

[30] Foreign Application Priority Data

Apr. 4, 1977 [JP] Japan .................. 52-38781
Apr. 25, 1977 [JP] Japan .................. 52-48900

[51] Int. Cl.$^3$ .................. C07C 41/00; C09F 5/00
[52] U.S. Cl. .................. 260/404; 568/618;
568/619; 564/123; 564/183; 564/184; 564/186;
564/189; 564/190; 564/192; 564/204; 564/207;
564/208; 564/215; 564/218; 564/223; 564/374;
564/383; 564/391; 564/392; 564/443; 564/453;
564/463; 564/505
[58] Field of Search .................. 260/404; 568/618, 619;
564/123, 183, 184, 186, 189, 190, 192, 204, 207,
208, 215, 218, 223, 374, 383, 391, 392, 443, 453,
463

[56] References Cited

U.S. PATENT DOCUMENTS 2,909,538 10/1959 Kirshenbaum .................. 260/409
3,040,076 6/1962 Seidel .................. 260/404
3,959,391 5/1976 Allain .................. 260/615 B

FOREIGN PATENT DOCUMENTS 967585 8/1964 United Kingdom .

OTHER PUBLICATIONS

Freedman et al. Tetrahedron Letters No. 38 pp. 3251-3254 (1975).

Primary Examiner—John F. Niebling
Attorney, Agent, or Firm—Burns, Doane, Swecker & Mathis

[57] ABSTRACT

Polyoxyalkylene compounds having at least four oxyalkylene units and one or two terminal hydroxyl groups are etherified by reacting same with organic primary chlorides or bromides in the presence of an aqueous, at least 30% by weight solution of sodium or potassium hydroxide to produce the corresponding etherified polyoxyalkylene derivatives. The molar ratio of the organohalide to the hydroxyl group(s) of the polyoxyalkylene compound is at least 1.2, and the molar ratio of the alkali metal hydroxide to such hydroxyl group(s) is at least 1.

35 Claims, No Drawings

PREPARATION OF ETHERIFIED POLYOXYALKYLENE DERIVATIVES

This is a continuation of application Ser. No. 867,621 filed Jan. 6, 1978 now abandoned.

BACKGROUND OF THE INVENTION

1. Field of the Invention

This invention relates to a process for preparing etherified polyoxyalkylene derivatives and, more particularly, relates to an improved process for preparing an etherified polyoxyalkylene derivative by etherifying a polyoxyalkylene compound having at least 4 oxyalkylene units and either one or two terminal hydroxyl groups through use of an organic primary halide and an aqueous solution of alkali metal hydroxide.

2. Description of the Prior Art

Etherification of a polyoxyalkylene compound having at least one terminal hydroxyl group has to date generally been effected by first reacting the polyoxyalkylene compound with an alkali metal or its hydride or alcoholate, such as sodium metal, potassium metal, sodium hydride or sodium hydride or sodium methylate, and then reacting the resultant alcoholate with an organic halide. This method enables the production of various etherified polyoxyalkylene derivatives. Concomitantly, however, the expensive alkali metal or its hydride or alcoholate is consumed stoichiometrically, and the yield of the desired product is at most 60%.

It is also known to prepare ethers of polyoxyalkylene glycol by reacting polyoxyalkylene glycol with an organic halide in the presence of a finely powdered alkali metal hydroxide at an elevated temperature, but this method cannot be conducted continuously and usually requires a higher temperature exceeding 100° C. to facilitate the reaction.

As a rather esoteric case, it is also known that polyoxyalkylene glycol diallyl ether can be produced by reacting polyoxyalkylene glycol with an allyl halide (per se well known as a highly reactive organic halide), even in the presence of an aqueous solution of alkali metal hydroxide. In this particular synthesis, a portion of the allyl halide is hydrolyzed and the yield of diallyl ether of polyoxyalkylene glycol is markedly low.

With regard to etherification by use of an aqueous solution of alkali metal hydroxide, it too is known to produce a polyoxyalkylene glycol dialkyl ether by reacting an aliphatic alcohol or mono-, di- or tri-oxyalkylene glycol monoalkyl ether with a β,β'-dihalogenodialkyl ether in the presence of an aqueous solution having a greater than 20 wt. % concentration of alkali metal hydroxide (German Pat. No. 1,129,147; British Pat. Specification No. 967,585). According to the specifications of the noted German and British patents, although the subject method affords the desired product, i.e., hexa- or octa-alkylene glycol diether, the yield is fairly low (about 58%), and a byproduct, i.e., tetra- or penta-alkylene glycol alkyl vinyl ether is formed in an about 30-40% yield. Since the polyoxyalkylene glycol diethers have a higher boiling point, it is virtually impossible to separate the desired product exclusively from the reaction mixture containing the desired product and high boiling byproducts.

In addition to the methods described above, the following methods for the etherification of polyoxyalkylene compounds having at least one terminal hydroxyl group are known: (i) a method comprising replacing the terminal hydroxyl group of the said polyoxyalkylene compound with a chlorine atom by reaction with thionyl chloride, followed by further reaction of the resultant chlorinated polyoxyalkylene compound with a metal alkoxide; (ii) a method comprising converting the terminal hydroxyl group of the said polyoxyalkylene compound into tosylate by reaction with a tosyl halide, i.e., p-toluene sulfohalide, and then further reacting the tosylate with an alkyl halide; (iii) a method of etherification with dialkyl sulfate; and (iv) a method of methyl etherification with formaldehyde. The methods (i) and (ii) are disadvantageous in view of requirement of two-stage reactions. Moreover, the raw materials used in these methods, i.e., thionyl chloride, metal alkoxide and tosyl halide, are too expensive from the viewpoint of their quantitative consumption. Dialkyl sulfate used in the method (iii) is also expensive and, for practical purposes, this synthesis is limited only to dimethyl sulfate which is extremely harmful to human health. The method (iv) is applicable only to methyl etherification.

SUMMARY OF THE INVENTION

According to the present invention, there is provided a process for preparing an etherified polyoxyalkylene derivative having the structural formula:

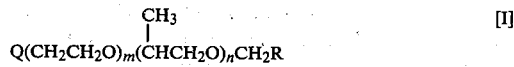
[I]

wherein m and n are each zero or numbers greater than zero, m and n not being both zero such that $m+n \geq 4$; Q is a member selected from $-OCH_2R$, $-OR^1$, $-N(CH_2R)R^2$, $-N(CH_2R)COR^2$, $-NR^2R^3$, $-N(R^3)COR^2$,

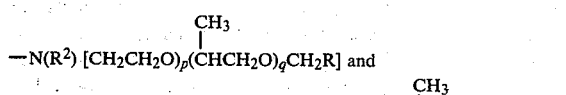

R is hydrogen or $-CR^4R^5R^6$; $R^1$, $R^2$ and $R^3$ are the same or different and are each a hydrocarbon group; $R^4$, $R^5$ and $R^6$ are each hydrogen or a hydrocarbon group; and p and q are each zero or numbers greater than zero such that $p+q>0$, which process comprises reacting a polyoxyalkylene compound having the general formula:

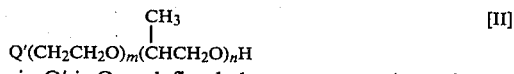
[II]

wherein Q' is Q as defined above or a member selected from $-OH$, $-NHR^2$, $-NHCOR^2$,

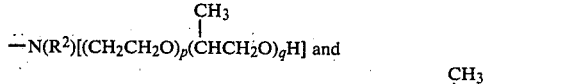

and m, n, $R^2$, p and q are as previously defined, with an organic halide having the general formula $$R-CH_2-X \qquad [III]$$

wherein X is chlorine or bromine and R is as previously defined, in the presence of an aqueous solution of sodium or potassium hydroxide having an initial alkali metal hydroxide concentration of at least 30% by weight, and at a molar ratio of the said organic halide to hydroxyl content of the said polyoxyalkylene compound of at least 1.2 and at a molar ratio of the said alkali metal hydroxide to hydroxyl content of the said polyoxyalkylene compound of at least 1.

DETAILED DESCRIPTION OF THE INVENTION

It has now been found that a polyoxyalkylene compound of the formula [II] (hereinafter referred to as the polyoxyalkylene compound [II]) can be easily etherified, virtually quantitatively, by reacting the polyoxyalkylene compound [II] with an organic halide of the formula [III] (hereinafter referred to as the organic halide [III]) under mild reaction conditions in the presence of an aqueous solution of sodium or potassium hydroxide, the initial concentration of the alkali metal hydroxide in the aqueous solution being at least 30% by weight.

It is well known to the art that the replacement reaction between an alcohol and an organic halide never or hardly ever proceeds in the presence of an aqueous solution of alkali metal hydroxide, except in those instances in which highly reactive halides, such as allylic halides, are used. It is, therefore, quite surprising that the reaction of the polyoxyalkylene compound [II] and the organic halide [III] can proceed smoothly, even in the presence of an aqueous solution of alkali metal hydroxide.

It is especially critical for the polyoxyalkylene compound [II] starting material to have at least four (preferably at least six) repeating oxyalkylene units so that the reaction may smoothly proceed. When such polyoxyalkylene compound [II] be employed, activation of the hydroxide anion is a characteristic result, and, consequently, the etherified product may be obtained almost quantitatively at an extremely high reaction rate. When polyoxyalkylene compounds having three or less oxyalkylene units are used, the foregoing effect may hardly appear, the reaction rate is generally too slow, and many undesirable side reactions may occur.

The process of the present invention possesses the following advantages over the known methods:

(a) A wide range of desired terminally etherified polyoxyalkylene derivatives can be produced by using an inexpensive and easy-to-handle aqueous solution of sodium or potassium hydroxide and a variety of organic halides which are common, readily available and less reactive;

(b) Quantitative etherification can be obtained through but a single stage reaction;

(c) Separation and purification of product are extremely easy; and (d) Symmetrical or asymmetrical etherified polyoxyalkylene derivatives of high purity can be obtained by varying the combination of the raw materials, the polyoxyalkylene compound [II] and the organic halide [III].

Other advantages of the process of the present invention will become clear from the following description.

The polyoxyalkylene compounds [II] used in the present invention include compounds of the following types:

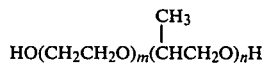
[II-a]

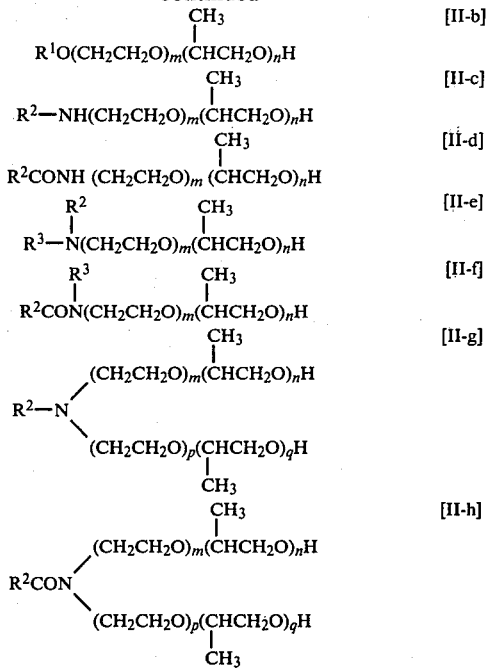

In the above structural formulae, $R^1$, $R^2$, $R^3$, m, n, p and q have the same meanings as defined hereinbefore. That is to say, $R^1$, $R^2$ and $R^3$ may be the same or different and are each hydrocarbon groups; m and n are zero or numbers greater than zero such that $m+n \geq 4$; and p and q are zero or numbers greater than zero such that $p+q>0$. Further, m and n are desirably values within the range, $4 \leq m+n \leq$ about 40, preferably within the range, $6 \leq m+n \leq 25$. Still further, p and q are desirably values within the range, $m+n+p+q \leq$ about 40, preferably within the range, $m+n+p+q \leq$ about 25. In polyoxyalkylene compounds which have both oxyethylene units and oxypropylene units in the same molecule, the orientation of the said oxyalkylene units is insignificant. They can be oriented in a random or block form. The number of carbon atoms in the hydrocarbon group, represented by $R^1$, $R^2$ and $R^3$, can range from 1 to about 20. Hydrocarbon groups suitable for $R^1$, $R^2$ and $R^3$ include, for example: saturated aliphatic hydrocarbon groups, such as methyl, ethyl, n-propyl, iso-propyl, n-butyl, n-amyl, isoamyl, n-hexyl, 2-methylpentyl, 2-ethylbutyl, n-heptyl, 2-methylhexyl, 2-ethylpentyl, 2,4-dimethylpentyl, n-octyl, 2-ethylhexyl, nonyl, 3-methyl-5-ethylhexyl, 3,5,5-trimethylhexyl, 2-ethyl-4,4-dimethylpentyl, n-decyl, 2,6-dimethyloctyl, 2,4,6-trimethylheptyl, undecyl, n-dodecyl, 3,5,5,7,7-pentamethyloctyl, 4,6,8-trimethylnonyl, cetyl, and stearyl; unsaturated aliphatic hydrocarbon groups, such as allyl, pentenyl, decenyl, and oleyl; cycloaliphatic hydrocarbon groups, such as cyclohexyl, methylcyclohexyl, and ethylcyclohexyl; substituted and unsubstituted phenyl groups, such as phenyl, butylphenyl, nonylphenyl, decylphenyl, undecylphenyl, and dodecylphenyl; and substituted and unsubstituted benzyl groups, such as benzyl, methylbenzyl, and nonylbenzyl. The hydrocarbon residues of synthetic alcohols obtained by the Ziegler process, the Oxo process or the paraffin oxidation process are included in the examples of suitable $R^1$, $R^2$ and $R^3$. These hydrocarbon groups can be replaced by different substituents within an innocuous range. It is preferred that the total number of carbon atoms in $R^2$ and $R^3$ be about 25 or less in the polyoxyalkylene compounds of the types [II-e] and [II-f]. The polyoxyalkylene compound [II] used in the present invention can be generally obtained by the (co)polymerization of ethylene oxide and-/or propylene oxide or by the (co)polyaddition of ethylene oxide and/or propylene oxide to the corresponding alcohol, amine or amide. Most of the polyoxyalkylene compounds [II] are produced commercially and are off-the-shelf items. From the viewpoint of usefulness of the product, the etherified polyalkylene derivative, the most preferred polyoxyalkylene compound to be used as a starting material is a polyoxyethylene compound of any of the foregoing types, especially type [II-a] or [II-b] which has from 4 to 20 (preferably from 6 to 13) oxyethylene units.

In the structural formula [III], R-CH$_2$-X, which represents the organic halide [III] used in this invention, R stands for hydrogen or the group, —CR$^4$R$^5$R$^6$. When R is the group, —CR$^4$R$^5$R$^6$, R$^4$, R$^5$ and R$^6$ are independently hydrogen or a hydrocarbon group. The said hydrocarbon group can, for example, be an alkyl, alkenyl, cycloalkyl, aryl, aralkyl or alkaryl group. The preferred total number of carbon atoms of R$^4$, R$^5$ and R$^6$ ranges between zero and about 20. It is especially preferred that two of R$^4$, R$^5$ and R$^6$ are each hydrogen or a lower alkyl group having from 1 to 4 carbon atoms. Preferred examples of the organic halide [III] include: saturated aliphatic chlorides and bromides having 1 to 18 carbon atoms, such as methyl chloride, methyl bromide, ethyl bromide, n-propyl chloride, n-propyl bromide, butyl chloride, butyl bromide, isoamyl chloride, isoamyl bromide, hexyl chloride, hexyl bromide, octyl chloride, octyl bromide, decyl chloride, decyl bromide, lauryl chloride, lauryl bromide, myristyl chloride, myristyl bromide, cetyl chloride, cetyl bromide, stearyl chloride, stearyl bromide, and the like; unsaturated aliphatic chlorides and bromides (except for the allylic chlorides and bromides), such as 9-decenyl chloride, 9-decenyl bromide, 9-dodecenyl chloride, 9-dodecenyl bromide, oleyl chloride, oleyl bromide, 9,12-octadecadienyl chloride, 9,12-octadecadienyl bromide and the like; and 2-cyclohexylethyl chloride, 2-cyclohexylethyl bromide, 2-phenylethyl chloride and 2-phenylethyl bromide, and the like. A variety of alkyl bromides and alkyl chlorides derived from synthetic alcohols, which are produced by the Ziegler process, the Oxo process or the paraffin oxidation process, are included in the preferred organic halides. The most preferred organic halides are saturated aliphatic primary chlorides and bromides having 5 to 18 carbon atoms.

When performing the process of the present invention, at least 1.2 moles of the organic halide [III] should be used per mole of the hydroxyl group of the polyoxyalkylene compound [II]. It is preferable to use from about 2 to about 5 moles of the organic halide [III] per mole of the hydroxyl group of the polyoxyalkylene compound [II]. It is usually desirable to complete the etherification of the polyoxyalkylene compound [II] by using the organic halide [III] in large excess, such that the organic halide additionally serves the function of reaction solvent.

In the process of the present invention, sodium hydroxide or potassium hydroxide (both could be used together) is used in the form of an aqueous solution having an initial alkali metal hydroxide concentration of at least 30% by weight, preferably from 40 to 75% by weight. When the initial concentration of alkali metal hydroxide is lower than 30% by weight in its aqueous solution, the reaction rate becomes much slower and the product is difficultly separable from the reaction mixture. As intended herein, the initial concentration of alkali metal hydroxide in its aqueous solution means the degree of its concentration upon the start of the reaction or upon use of the said aqueous solution. The molar ratio of alkali metal hydroxide to hydroxyl group of the polyoxyalkylene compound [II] should be at least 1 and is preferably in the range of from about 1.5 to about 5. As the reaction proceeds, the alkali metal hydroxide is consumed. Although it is possible to supply an additional amount of alkali metal hydroxide during the reaction, this is usually unnecessary except in that event in which the alkali metal hydroxide is supplied together with the raw materials, the polyoxyalkylene compound [II] and the organic halide [III].

According to the present invention, the reaction is carried out by agitating the heterogeneous mixture consisting essentially of the polyoxyalkylene compound [II], the organic halide [III] and the aqueous solution of alkali metal hydroxide. With a view to facilitating the separation of product from the reaction mixture, the reaction may be carried out in the co-existence or simultaneous presence of an organic solvent which is chemically stable in this reaction system but which is not freely soluble in water. Examples of operable solvents include: hydrocarbons such as hexane, heptane, octane, cyclohexane, benzene, toluene, xylene, and the like; substituted benzenes such as chlorobenzenes and benzonitrile; and ethers such as dibutyl ether, anisole, and the like. There is no special limitation on the amount of these organic solvents to be used. From the viewpoint of reaction efficiency and economy, however, it is desirable to set the volume ratio between the aqueous phase and the organic phase in the reaction system within a range of from 5:1 to 1:10. The reaction temperature generally ranges from about 20° C. to about 150° C., preferably from 50° C. to 120° C. The optimum reaction temperature varies depending on the type of the raw materials, particularly of the organic halide [III]. In a preferred embodiment of the present invention, the reaction is carried out at the boiling point of organic halide and/or solvent in order to remove the heat of reaction by refluxing same. The etherification reaction is usually performed under atmospheric pressure. When an organic halide having a very low boiling point like methyl bromide or ethyl chloride is used, it is desirable to carry out the reaction under an increased pressure from the viewpoint of the reaction rate. The etherification reaction according to the present invention is carried out preferably under a nitrogen gas atmosphere or other inert gas atmosphere so that coloration of the product can be minimized. Even when the reaction is performed under the inert gas atmosphere, a colored product is occasionally formed. In such a case, the coloration of the product can be reduced or virtually eliminated by hydrogenation of the product. This hydrogenation treatment is advantageously performed by subjecting the etherified product to contact with molecular hydrogen (H$_2$) for from several hours to about 20 hours in the presence of from about 0.1 to about 10% by weight (based on the weight of the etherified polyoxyalkylene derivative) of a hydrogenation catalyst such as Raney nickel, nickel on diatomaceous earth, palladium black, palladium on carbon, palladium on silica, platinum black or a supported platinum catalyst, and in the absence or, preferably, the presence of a substantially inert solvent (for example, water; alcohols, such as methanol, ethanol, propanol and butanol; ethers, such as tetrahydrofuran, dioxane and diethylene glycol dimethyl ether; and hydrocarbons, such as hexane, heptane, octane, cyclohexane, benzene, toluene and xylene), at a temperature ranging from room temperature to 200° C., preferably at 50° C. to 150° C., under a hydrogen pressure of from 1 to 200 atomspheres, preferably 1 to 100 atmospheres.

It has also been found that a but slightly colored or virtually colorless product can be obtained when the raw material, the polyoxyalkylene compound [II], is pre-treated with hydrogen under the same conditions as discussed immediately above in the presence of the hydrogenation catalyst and then this hydrogenation product is employed for the etherification reaction according to the present invention, or when the etherification reaction is carried out in the presence of an inorganic reducing agent. Exemplary inorganic reducing agents include: sodium sulfide, potassium sulfide, sodium sulfite, potassium sulfite, sodium polysulfide, ammonium sulfide, sodium thiosulfate, sodium hypochlorite, phosphorus trisulfide, sodium phosphite, sodium pyrosulfite, potassium pyrosulfite, sodium formate, potassium formate, hydrazine hydrate, hydrogen sulfide, stannous chloride, ferrous sulfate, ferrous hydroxide, cuprous hydroxide, sodium nitrite and potassium nitrite. The optimum amount of the inorganic reducing agent is generally within the range of from about 0.05 to about 10 % by weight based on the weight of the polyoxyalkylene compound [II].

In the present invention, the reaction between the polyoxyalkylene compound [II] and the organic halide [III] can be carried out either batchwise or in a continuous manner. The resulting product can be recovered from the reaction mixture by conventional methods and procedures for separation. For example, when the etherified polyoxyalkylene derivatives are less soluble in water, they can be isolated as a residue by the steps comprising separating the reaction mixture into an aqueous layer and an organic layer, adding a solvent insoluble in water to the said organic layer wherever necessary, completely washing the said organic layer with water, and then removing the solvent, unreacted organic halide remaining, and low boiling byproducts from the organic layer. When the etherified polyoxyalkylene derivatives are relatively soluble in water, they can be isolated by the steps comprising neutralizing the reaction mixture with an acid, evaporating water from the mixture, removing precipitated inorganic salt from the mixture by filtraton at an elevated temperature, and evaporating the remaining lower boiling compounds from the filtrate, if necessary. In this case, the organic solvent and the unreacted organic halide contained in the reaction mixture can be removed simultaneously with or prior to the removal of water, or after filtration, according to their respective physical properties.

The etherified polyoxyalkylene derivatives produced by the process of the present invention are chemical compounds shown in the foregoing general formula [I] and are any of the following types corresponding to the polyoxyalkylene compound [II] employed as starting material:

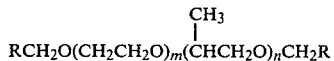

$$RCH_2O(CH_2CH_2O)_m(CHCH_2O)_nCH_2R \quad [I\text{-}a]$$

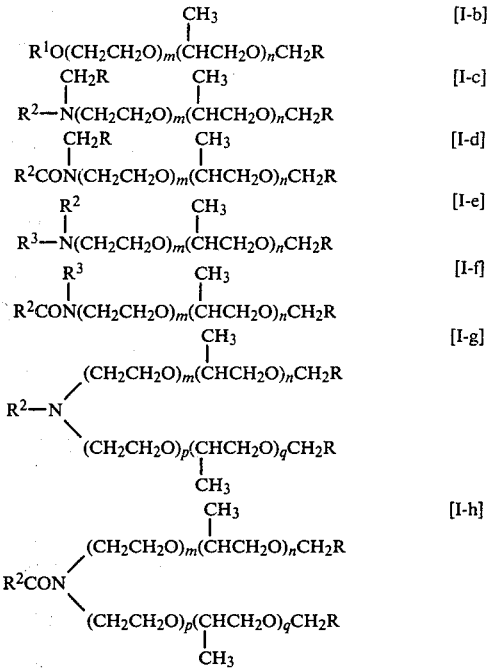

In the above structural formulae, R, $R^1$, $R^2$, $R^3$, m, n, p and q have the meanings as defined hereinbefore.

When the polyoxyalkylene compound [II] of the type [II-c] or [II-d] be utilized, the etherified product of the following types: [I-c'] or [I-d'], respectively, may occasionally be formed together with, or in place of, the etherified product of the types [I-c] or [I-d], respectively:

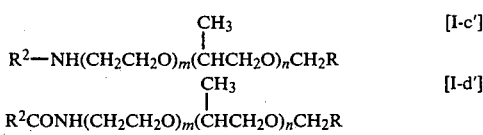

In the above structural formulae, R, $R^2$, m and n have the meanings as defined hereinbefore.

Depending on the type of their terminal groups, the etherified polyoxyalkylene derivatives produced by the process of the present invention are useful as surface active agents, solvents, solubilizing agents for inorganic salts, accelerators or catalysts for ionic organic reactions, for example.

In order to further illustrate the invention and the advantages thereof, the following specific examples are given, it being understood that the same are intended only as illustrative, and in nowise limitative.

In the following examples, polyoxyethylene glycol and polyoxypropylene glycol are referred to as polyethylene glycol and polypropylene glycol, respectively.

EXAMPLE 1

Into a 1-liter four-necked, round bottomed flask equipped with a thermometer, a reflux condenser and a mechanical stirrer, were placed 97 g of tetraethylene glycol, $HO(C_2H_4O)_4H$, 411 g of n-butyl bromide, 1 g of sodium thiosulfate and 240 g of 50 wt. % aqueous sodium hydroxide solution. The mixture was vigorously stirred at 90° C. for 5 hours under a nitrogen atmosphere. After completion of the reaction, the mixture was cooled to room temprature. The mixture was separated into organic and aqueous layers by using a separatory funnel. The organic layer was distilled under reduced pressure to recover part of n-butyl bromide (appox. 200 g). After distillation, 500 ml of n-hexane was added to the organic layer. The organic layer was then washed twice with 300 ml of water and dried over anhydrous sodium sulfate. The solid material was removed from the organic layer by filtration. The organic layer was then subjected to distillaton to remove n-hexane, n-butyl bromide and lower-boiling substances and there were obtained 151 g of colorless liquid as a residue. Gas chromatographic analysis showed that the colorless liquid consisted substantially of tetraethylene glycol di-n-butyl ether and contained neither tetraethylene glycol nor tetraethylene gklycol mono-n-butyl ether therein.

Yield of the tetraethylene glycol di-n-butyl ether based on the tetraethylene glycol charged: 99%

Yield of the tetraethylene glycol di-n-butyl ether based on the n-butyl bromide reacted: 95%

Transmittance at wave length of 450 nm (cell width; 1cm): 99%.

Byproducts were 4% of n-butene and 1% of di-n-butyl ether (both based on the reacted n-butyl bromide).

EXAMPLE 2

Into the same flask as in Example 1 were placed 300 ml of benzene, 100 g of polyethylene glycol (average molecular weight; 400), 300 g of 2-ethylhexyl bromide, 5 g of sodium sulfite and 130 g of 60 wt. % aqueous sodium hydroxide solution. The mixture was refluxed for 9 hours under a nitrogen atmosphere with vigorously stirring. After the reaction, the reaction mixture was treated in the same manner as in Example 1to obtain 151 g of colorless liquid as a residue. Neither polyethylene glycol nor polyethylene glycol mono-2-ethylhexyl ether was detected in gas chromatographic analyis of the colorless liquid. Part of the polyethylene glycol di-2-ethylhexyl ether obtained was made into a 20 % benzene solution, the light transmittance of which was measured in a 10 cm width cell at wave length of 450 nm and determined to be 98%.

Yield of the polyethylene glycol diether based on the polyethylene glycol charged: 97%.

Yield of the polyethylene glycol diether based on the 2-ethylhexyl bromide reacted: 96%.

EXAMPLE 3

Into the same flask as in Example 1 were placed 175 g of polyethylene glycol mono-2-ethylhexyl ether (average molecular weight; 350), 250 g of 3,5,5-trimethylhexyl chloride, 120 g of 60 wt. % aqueous sodium hydroxide solution and 1 g of sodium nitrite. The mixture was vigorously stirred at 100° C. for 10 hours under a nitrogen atmosphere. After completion of the reaction, the reaction mixture was treated in the same manner as in Example 1 to obtain 210 g of polyethylene glycol 2-ethylhexyl 3,5,5-trimethylhexyl ether (average molecular weight was 476, yield based on the polyethylene glycol mono-2-ethylhexyl ether charged was 90%).

EXAMPLE 4

Into the same flask as in Example 1 were placed 200 ml of monochlorobenzene,

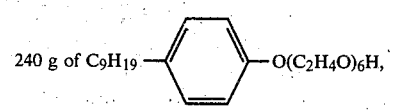

240 g of n-hexyl chloride and 280 g of 50 wt. % aqueous potassium hydroxide solution, and the mixture was vigorously stirred at 100° C. for 15 hours under a nitrogen atmosphere. After completion of the reaction, the reaction mixture was treated in the same manner as in Example 1 to obtain 280 g of pale yellow liquid as a residue. To 2.0 g of the residue was added 10 ml of 10 wt. % trimethyl aluminum benzene solution. The amount of methane evolved was 0.2 millimole. This result, together with gas chromatographic analysis, indicated that the reaction mixture contained 264 g of

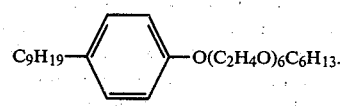

The transmittance was measured in the same manner as in Example 2 to be 80%.

COMPARATIVE EXAMPLE 1

Into the same flask as in Example 1 were placed 200 ml of benzene, 50 g of diethylene glycol, 340 g of n-butyl bromide and 200 g of 50 wt. % aqueous potassium hydroxide solution, and the mixture was refluxed for 15 hours under a nitrogen atmosphere with vigorously stirring. After completion of the reaction, the reaction mixture was extracted with n-butanol. Analysis of the n-butanol layer by means of gas chromatography showed that the yield of diethylene glycol di-n-butyl ether produced was only 15% and the yield of diethylene glycol mono-n-butyl ether was 38% (both yields based on the diethylene glycol charged).

EXAMPLE 5

Into a 500-ml autoclave were placed 100 g of commercial polyethylene glycol (average molecular weight; 300), 100 g of water and 3 g of nickel or diatomaceous earth catalyst (nickel content; 50 wt. %). The mixture was hydrogenated at 100° C. for 2 hours under a hydrogen pressure of 50 atm with vigorously stirring. One hundred grams (100 g) of the hydrogenated polyethylene glycol were placed in the same flask as in Example 1, and 160 g of 50 wt. % aqueous sodium hydroxide solution and 380 g of n-octyl bromide were further added thereto. The mixture was vigorously stirred at 90° C. under a nitrogen atmosphere for 5 hours. After the reaction, the reaction mixture was treated in the same manner as in Example 1 to obtain 175 g of polyethylene glycol di-n-octyl ether as a residue. In gas chromatographic analysis of the residue, neither polyethylene glycol nor polyethylene glycol mono-n-octyl ether was detected. The transmittance of the product measured in the same manner as in Example 2 was 99.5%.

EXAMPLE 6

Example 5 was repeated except that polyethylene glycol (average molecular weight; 300) in the same lot as used in Example 5 was not hydrogenated. As a result, 173 g of polyethylene glycol di-n-octyl ether were obtained. The transmittance of the product measured in the same manner as in Example 2 was 59%.

Into a 1-liter autoclave were placed 100 g of the above crude polyethylene glycol di-n-octyl ether, 600 ml of ethanol and 3 g of nickel of diatomaceous earth catalyst (nickel content; 50%), and the mixture was hydrogenated at 100° C. under a hydrogen pressure of 50 atm with vigorously stirring for 3 hours. After completion of the reaction, the catalyst was removed from the reaction mixture by filtration and then ethanol was distilled off to obtain 99 g of colorless polyethylene glycol di-n-octyl ether as a residue. Light transmittance of the product was also measured in the same manner as in Example 5 to be 98%.

COMPARATIVE EXAMPLE 2

Into the same flask as in Example 1 were placed 300 ml of benzene, 70 g of polyethylene glycol, HO(C$_2$H$_4$O)$_{6.5}$H (average molecular weight; 300), 300 g of 15 wt.% aqueous sodium hydroxide solution and 170 g of n-butyl bromide, and the mixture was refluxed for 9 hours under a nitrogen atmosphere with vigorously stirring. After the reaction, gas chromatographic analysis indicated that the organic layer separated from the reaction mixture contained only 2 g of n-C$_4$H$_9$O(CH$_2$C-H$_2$O)$_{6.5}$n-C$_4$H$_9$.

EXAMPLE 7

Into the same flask as in Example 1 were placed 150 ml of monochlorobenzene, 200 g of polypropylene glycol (average molecular weight; 2,000), 120 g of 3,5,5-trimethylhexyl chloride, 2 g of sodium nitrite and 65 g of 60 wt. % aqueous sodium hydroxide solution, and the mixture was rapidly stirred at 100° C. under a nitrogen atmosphere for 15 hours. After completion of the reaction, the reaction mixture was treated in the same manner as in Example 1 to obtain 215 g of transparent polypropylene glycol die-3,5,5-trimethylhexyl ether as a residue.

EXAMPLE 8

Into the same flask as in Example 1 were placed 125 g of

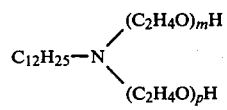

(average number of oxyethylene units; 10), 300 g of 2-ethylhexyl bromide, 2 g of sodium thiosulfate and 130 g of 50 wt. % aqueous sodium hydroxide solution, and the mixture was rapidly stirred at 80° C. under a nitrogen atmosphere for 8 hours. After the reaction, the reaction mixture was treated in the same manner as in Example 1 to obtain 165 g of

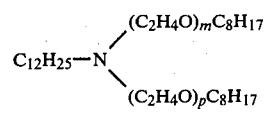

as a residue. Analysis by means of gel permeation chromatography showed that the average molecular weight of the residue was 850, while no bromine was detected in the elemental analysis of the residue.

EXAMPLE 9

Into the same flask as in Example 1 was placed 100 ml of dibutyl ether, 100 g of n-butyl bromide, 2 g of potassium thiosulfate, 75 g of 60 wt. % aqueous potassium hydroxide solution and 120 g of

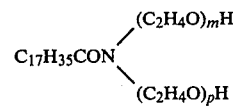

(average number of oxyethylene units; 20), and the mixture was reacted 80° C. under a nitrogen atmosphere for 10 hours with rapid stirring. After completion of the reaction, the reaction mixture was separated into organic and aqueous layers. Two hundred (200) milliliters of n-butanol was added to the organic layer, which was then washed twice with 300 ml of water. The organic layer was treated in the same manner as in Example 1 to obtain 128 g of

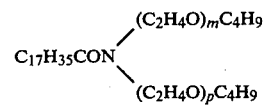

as a residue. The average molecular weight of the product was confirmed by means of gel permeation chromatography to be 1,275 and absorption at 1650 cm$^{-1}$ was observed in its infrared spectrum.

EXAMPLES 10-22

The etherification reaction of various polyoxyalkylene compounds with various organic halides under varying conditions produced the corresponding etherified polyoxyalkylene derivatives. The reaction in Examples 17 and 22 was carried out by using a 1-liter autoclave, while the reaction in Examples 10-16 and 18-21 was performed by using the same flask as in Example 1. The results are summarized in the following Table I:

TABLE I

| Example | Starting Material Polyoxyalkylene compound | Halide | Aqueous solution of alkali metal hydroxide | Solvent |
|---|---|---|---|---|
| 10 | CH$_3$O(C$_2$H$_4$O)$_{6.5}$H (100 g) | N-C$_8$H$_{17}$Br (250 g) | 30% NaOH (170 g) | — |
| 11 | CH$_3$O(C$_2$H$_4$O)$_{6.5}$H (100 g) | n-C$_8$H$_{17}$Br (250 g) | 70% NaOH (73 g) | — |
| 12 | CH$_3$O(C$_2$H$_4$O)$_{6.5}$H (100 g) | n-C$_8$H$_{17}$Br (250 g) | 50% NaOH (102 g) | — |
| 13 | CH$_3$O(C$_2$H$_4$O)$_{6.5}$H (100 g) | n-C$_8$H$_{17}$Br (250 g) | 50% KOH (143 g) | — |
| 14 | CH$_3$O(C$_2$H$_4$O)$_{6.5}$H (100 g) | n-C$_8$H$_{17}$Br (61 g) | 50% NaOH (102 g) | — |

TABLE I-continued

| | | | | |
|---|---|---|---|---|
| 15 | CH$_3$O(C$_2$H$_4$O)$_{6.5}$H (100 g) | n-C$_8$H$_{17}$Br (130 g) | 50% NaOH (102 g) | — |
| 16 | HO(C$_2$H$_4$O)$_{8.7}$H (80 g) | n-C$_{18}$H$_{37}$Br (400 g) | 60% KOH (150 g) | C$_6$H$_5$Cl (200 ml) |
| 17 | HO(C$_2$H$_4$O)$_{8.7}$H (100 g) | C$_2$H$_5$Cl (130 g) | 60% KOH (230 g) | — |
| 18 | HO(C$_2$H$_4$O)$_m$(CHCH$_2$O)$_n$H with CH$_3$ branch (Mw=1650, m/n=40/60) (80 g) | n-C$_{18}$H$_{35}$Br (100 g) | 50% NaOH (40 g) | C$_6$H$_5$OCH$_3$ (100 ml) |
| 19 | n-C$_4$H$_9$O(C$_2$H$_4$O)$_m$—(CHCH$_2$O)$_n$H with CH$_3$ branch (Mw=1400, m/n=40/60) (70 g) | iso-C$_5$H$_{11}$Cl (100 g) | 50% NaOH (40 g) | C$_6$H$_5$CN (100 ml) |
| 20 | C$_6$H$_5$O(C$_2$H$_4$O)$_{15}$H (150 g) | C$_6$H$_{11}$CH$_2$Br (106 g) | 60% NaOH (130 g) | — |
| 21 | C$_{12}$H$_{25}$NH(C$_2$H$_4$O)$_5$H (100 g) | n-C$_4$H$_9$Cl (140 g) | 60% NaOH (140 g) | C$_6$H$_6$ (100 ml) |
| 22 | C$_{18}$H$_{37}$NH(C$_2$H$_4$O)$_{10}$H (70 g) | CH$_3$Br (76 g) | 50% NaOH (64 g) | (C$_4$H$_9$)$_2$O (100 ml) |

| Example | Reducing Agent | Conditions | Yield based on polyoxyalkylene compound charged |
|---|---|---|---|
| 10 | — | 80° C., 15 hrs. | 92% CH$_3$O(C$_2$H$_4$O)$_{6.5}$n-C$_8$H$_{17}$ |
| 11 | — | 80° C., 4 hrs. | 99% CH$_3$O(C$_2$H$_4$O)$_{6.5}$n-C$_8$H$_{17}$ |
| 12 | — | 80° C., 6 hrs. | 99% CH$_3$O(C$_2$H$_4$O)$_{6.5}$n-C$_8$H$_{17}$ |
| 13 | — | 80° C., 6 hrs. | 99% CH$_3$O(C$_2$H$_4$O)$_{6.5}$n-C$_8$H$_{17}$ |
| 14 | — | 80° C., 8 hrs. | 72% CH$_3$O(C$_2$H$_4$O)$_{6.5}$n-C$_8$H$_{17}$ |
| 15 | — | 80° C., 8 hrs. | 98% CH$_3$O(C$_2$H$_4$O)$_{6.5}$n-C$_8$H$_{17}$ |
| 16 | FeSO$_4$·5H$_2$O (0.5 g) | 90° C., 6 hrs. | 99% n-C$_{18}$H$_{37}$O(C$_2$H$_4$O)$_{8.7}$n-C$_{18}$H$_{37}$ |
| 17 | KNO$_2$ (0.5 g) | 90° C., 10 hrs. | 92% C$_2$H$_5$O(C$_2$H$_4$O)$_{8.7}$C$_2$H$_5$ |
| 18 | Na$_2$SO$_3$ (1 g) | 90°C., 7 hrs. | 99% n-C$_{18}$H$_{35}$O(C$_2$H$_4$O)$_m$—(CHCH$_2$O)$_n$n-C$_{18}$H$_{35}$ with CH$_3$ branch |
| 19 | Na$_2$SO$_3$ (1 g) | 100° C., 10 hrs. | 98% n-C$_4$H$_9$O(C$_2$H$_4$O)$_m$—(CHCH$_2$O)$_n$iso-C$_5$H$_{11}$ with CH$_3$ branch |
| 20 | KH$_2$PO$_3$·2H$_2$O (1.5 g) | 80° C., 6 hrs. | 99% C$_6$H$_5$O(C$_2$H$_4$O)$_{15}$CH$_2$C$_6$H$_{11}$ |
| 21 | Na$_2$SO$_3$ (1.5 g) | 80° C., 14 hrs. | 96% C$_{12}$H$_{25}$N(C$_2$H$_4$O)$_5$n-C$_4$H$_9$ with C$_4$H$_9$ branch |
| 22 | — | 70° C., 8 hrs. | 97% C$_{18}$H$_{37}$N(C$_2$H$_4$O)$_{10}$CH$_3$ with CH$_3$ branch |

While the invention has been described in terms of various preferred embodiments, the skilled artisan will appreciate that various embodiments, substitutions, omissions, and changes may be made without departing from the spirit thereof. Accordingly, it is intended that the scope of the present invention be limited solely by the scope of the following claims.

What is claimed is:

1. A process for preparing an etherified polyoxyalkylene derivative having the structural formula:

$$Q(CH_2CH_2O)_m(CHCH_2O)_nCH_2R \qquad [I]$$

with CH$_3$ branch wherein m and n are zero or numbers greater than zero, m and n not being both zero, such that m+n≧4; Q is a member selected from the group consisting of —OCH$_2$R, —OR$^1$, —N(CH$_2$R)R$^2$, —N(CH$_2$R)COR$^2$, —NR$^2$R$^3$, —N(R$^3$)COR$^2$, $$—N(R^2)[(CH_2CH_2O)_p(CHCH_2O)_qCH_2R] \text{ with } CH_3 \text{ branch, and}$$

$$—N(COR^2)[(CH_2CH_2O)_p(CHCH_2O)_qCH_2R] \text{ with } CH_3 \text{ branch};$$

R is hydrogen or —CR$^4$R$^5$R$^6$; R$^1$, R$^2$ and R$^3$ are the same or different and are each a hydrocarbon; R$^4$, R$^5$ and R$^6$ are each hydrogen or a hydrocarbon; and p and q are each zero or numbers greater than zero such that p+q>0, which process consists essentially of reacting in a single step a polyoxyalkylene compound having the structural formula:

$$Q'(CH_2CH_2O)_m(CHCH_2O)_nH \qquad [II]$$

with CH$_3$ branch wherein Q' is Q as defined above or a member selected from —OH, —NHR$^2$, —NHCOR$^2$, —N(R²)[(CH₂CH₂O)$_p$(CHCH₂O)$_q$H] and $$-N(COR^2)[(CH_2CH_2O)_p(CHCH_2O)_qH]\overset{|}{\underset{}{CH_3}};$$

and m, n, R², p and q are as previously defined, with an organic halide having the structural formula:

R—CH₂—X [III]

wherein X is chlorine or bromine atom and R is as previously defined, in the presence of an aqueous solution of sodium or potassium hydroxide having an initial alkali metal hydroxide concentration of from about 30% to about 75% by weight, and at a molar ratio of the said organic halide to hydroxyl content of the said polyoxyalkylene compound of at least 1.2 and at a molar ratio of the said alkali metal hydroxide to hydroxyl content of the said polyoxyalkylene compound of at least 1.

2. The process as defined by claim 1, wherein the polyoxyethylene compound [II] has the structural formula:

$$HO(CH_2CH_2O)_m(\overset{CH_3}{\underset{|}{C}}HCH_2O)_nH.$$

3. The process as defined by claim 1, wherein the polyoxyethylene compound [II] has the structural formula:

$$R^1O(CH_2CH_2O)_m(\overset{CH_3}{\underset{|}{C}}HCH_2O)_nH.$$

4. The process as defined by claim 1, wherein the polyoxyethylene compound [II] has the structural formula:

$$R^2—NH(CH_2CH_2O)_m(\overset{CH_3}{\underset{|}{C}}HCH_2O)_nH.$$

5. The process as defined by claim 1, wherein the polyoxyethylene compound [II] has the structural formula:

$$R^2CONH(CH_2CH_2O)_m(\overset{CH_3}{\underset{|}{C}}HCH_2O)_nH.$$

6. The process as defined by claim 1, wherein the polyoxyethylene compound [II] has the structural formula:

$$R^3—\overset{R^2}{\underset{|}{N}}(CH_2CH_2O)_m(\overset{CH_3}{\underset{|}{C}}HCH_2O)_nH.$$

7. The process as defined by claim 1, wherein the polyoxyethylene compound [II] has the structural formula:

$$R^2CON(CH_2CH_2O)_m(\overset{CH_3}{\underset{|}{C}}HCH_2O)_nH.$$ (with R³ on N)

8. The process as defined by claim 1, wherein the polyoxyethylene compound [II] has the structural formula:

$$R^2—N\begin{matrix}(CH_2CH_2O)_m(\overset{CH_3}{\underset{|}{C}}HCH_2O)_nH\\ \\(CH_2CH_2O)_p(\overset{}{\underset{|}{C}}HCH_2O)_qH\\CH_3\end{matrix}.$$

9. The process as defined by claim 1, wherein the polyoxyethylene compound [II] has the structural formula:

$$R^2CON\begin{matrix}(CH_2CH_2O)_m(\overset{CH_3}{\underset{|}{C}}HCH_2O)_nH\\ \\(CH_2CH_2O)_p(\overset{}{\underset{|}{C}}HCH_2O)_qH\\CH_3\end{matrix}.$$

10. The process as defined by claim 1, wherein the values of m and n are within the range, $4 \leq m+n \leq$ about 40.

11. The process as defined by claim 1, wherein the values of m and n are with the range, $6 \leq m+n \leq 25$.

12. The process as defined by claim 1, wherein the values of m, n, p and q are within the range, $m+n+p+q \leq$ about 40.

13. The process as defined by claim 1, wherein the values of m, n, p and q are within the range $m+n+p+q \leq$ about 25.

14. The process as defined by claim 1, wherein the hydrocarbon groups R¹, R², R³, R⁴, R⁵ and R⁶ have from 1 to 20 carbon atoms.

15. The process as defined by claim 1, wherein each hydrocarbon R¹, R² and R³ is selected from the group consisting of methyl, ethyl, n-propyl, iso-propyl, n-butyl, n-amyl, isoamyl, n-hexyl, 2-methylpentyl, 2-ethylbutyl, n-heptyl, 2-methylhexyl, 2-ethylpentyl, 2,4-dimethylpentyl, n-octyl, 2-ethylhexyl, nonyl, 3-methyl-5-ethylhexyl, 3,5,5-trimethylhexyl, 2-ethyl-4,4-dimethylpentyl, n-decyl, 2,6-dimethyloctyl, 2,4,6-trimethylheptyl, undecyl, n-dodecyl, 3,5,5-7,7-pentamethyloctyl, 4,6,8-trimethylnonyl, cetyl, stearyl, allyl, pentenyl, decenyl, oleyl, cyclohexyl, methylcyclohexyl, ethylcyclohexyl, phenyl, butylphenyl, nonylphenyl, decylphenyl, undecylphenyl, dodecylphenyl, benzyl, methylbenzyl, and nonylbenzyl.

16. The process as defined by claim 1, wherein the polyoxyalkylene compoound of the structural formula [II] is a polyoxyethylene compound having from 4 to 20 oxyethylene units and the organic halide of the structural formula [III] is a saturated aliphatic chloride or bromide having from 5 to 18 carbon atoms.

17. The process as defined by claim 16, wherein the polyoxyethylene compound is polyoxyethylene glycol.

18. The process as defined by claim 16, wherein the polyoxyethylene compound is a polyoxyethylene compound is a polyoxyethylene glycol monoether.

19. The process as defined by claim 1, wherein the reaction is carried out in the presence of an inorganic reducing agent.

20. The process as defined by claim 1, wherein the polyoxyalkylene compound of the general formula [II] is hydrogenated prior to reaction with the organic halide [III].

21. The process as defined by claim 1, wherein the reaction temperature ranges from about 20° C. to about 150° C.

22. The process as defined by claim 21, wherein the reaction temperature ranges from 50° C. to 120° C.

23. The process as defined by claim 1, wherein the initial concentration of alkali metal hydroxide in the aqueous solution is in the range of from 40% to 75% by weight.

24. The process as defined by claim 1, wherein the molar ratio of the organic halide to hydroxyl content of the polyoxyalkylene compound is in the range of from about 2 to about 5.

25. The process as defined by claim 1, further comprising hydrogenating the resultant etherified polyoxyalkylene derivative [I].

26. The process as defined by claim 1, wherein the reaction is conducted in the presence of an inert organic solvent.

27. The process as defined by claim 1, wherein the reaction is conducted under an atmosphere of an inert gas.

28. The process as defined by claim 19, wherein the reducing agent is employed in amounts of from about 0.05 to about 10% by weight, based on the weight of the polyoxyalkylene compound [II].

29. The process as defined by claim 1, wherein the reaction is carried out batchwise.

30. The process as defined by claim 1, wherein the reaction is carried out continuously.

31. The process as defined by claim 1, wherein the product etherified polyoxyalkylene derivative [I] is selected from the group consisting of those of the structural formulae:

$$RCH_2O(CH_2CH_2O)_m(\overset{\underset{\mid}{CH_3}}{C}HCH_2O)_nCH_2R;$$

$$R^1O(CH_2CH_2O)_m(\overset{\underset{\mid}{CH_3}}{C}HCH_2O)_nCH_2R;$$

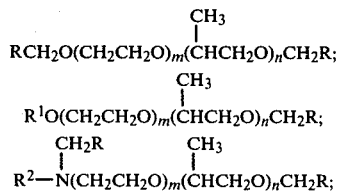

-continued

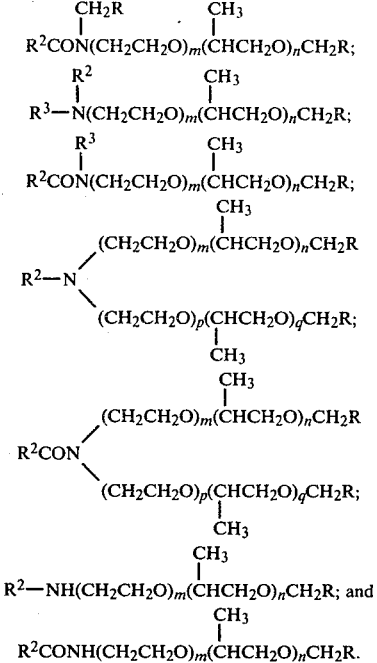

32. The process as defined by claim 1, wherein the polyoxyalkylene compound of the structural formula [II] has at least 6 repeating oxyalkylene units.

33. The process as defined by claim 1, wherein the total number of carbon atoms in $R^2$ and $R^3$ is no greater than 25.

34. The process as defined by claim 1, wherein the organic halide [III] is $X$-$CH_2$-$CR^4R^5R^6$, in which each $R^4$, $R^5$ and $R^6$ is either hydrogen or a hydrocarbon having up to 20 carbon atoms selected from the group consisting of alkyl, alkenyl, cycloalkyl, aryl, aralkyl and alkaryl.

35. The process as defined by claim 1, wherein the organic halide [III] is selected from the group consisting of methyl chloride, methyl bromide, ethyl bromide, n-propyl chloride, n-propyl bromide, butyl chloride, butyl bromide, isoamyl choride, isoamyl bromide, hexyl chloride, hexyl bromide, octyl chloride, octyl bromide, decyl chloride, decyl bromide, lauryl chloride, lauryl bromide, myristyl chloride, myristyl bromide, cetyl chloride, cetyl bromide, stearyl chloride, stearyl bromide, 9-decenyl bromide, 9-dodecenyl chloride, 9-dodecenyl bromide, oleyl chloride, oleyl bromide, 9,12-octadecadienyl chloride, 9,12-octadecadienyl bromide, 2-cyclohexylethyl chloride, 2-cyclohexylethyl bromide, 2-phenylethyl chloride and 2-phenylethyl bromide.

* * * * *